United States Patent [19]
Deno

[11] Patent Number: 4,598,417
[45] Date of Patent: Jul. 1, 1986

[54] ELECTRONIC STETHOSCOPE

[75] Inventor: Norman S. Deno, State College, Pa.

[73] Assignee: Research Corporation, N.Y.

[21] Appl. No.: 641,130

[22] Filed: Aug. 15, 1984

[51] Int. Cl.$^4$ .................. A61B 7/04; H03F 21/00; H04R 3/04; H04R 19/01
[52] U.S. Cl. .................. 381/67; 179/111 E; 181/131; 381/95; 381/96; 381/121
[58] Field of Search .......... 381/67, 95, 96, 121; 128/715, 696; 181/126, 131; 179/111 E

[56] References Cited
U.S. PATENT DOCUMENTS

| | | | |
|---|---|---|---|
| 3,321,041 | 5/1967 | Bowen, Jr. ................ | 181/131 |
| 3,525,810 | 8/1970 | Adler . | |
| 3,764,748 | 10/1973 | Branch et al. . | |
| 3,989,895 | 11/1976 | O'Daniel, Jr. ............. | 381/67 |
| 3,989,904 | 11/1976 | Rohrer et al. . | |
| 4,220,160 | 9/1980 | Kimball et al. . | |
| 4,548,082 | 10/1985 | Engebretson et al. . | |

FOREIGN PATENT DOCUMENTS

| | | | |
|---|---|---|---|
| 36230 | 9/1981 | European Pat. Off. ........... | 381/96 |
| 2141141 | 2/1973 | Fed. Rep. of Germany ....... | 381/96 |
| 622207 | 8/1978 | U.S.S.R. ........................ | 381/95 |

Primary Examiner—Gene Z. Rubinson
Assistant Examiner—Danita R. Byrd
Attorney, Agent, or Firm—Scully, Scott, Murphy & Presser

[57] ABSTRACT

An electronic stethoscope for reproducing at a user's ear as exactly as possible the sound pressure signals originating from a conventional diaphragm or bell type of chestpiece. The subject electronic stethoscope utilizes a signal processing approach which relies upon acousto-electronic feedback to provide an error or adjustment signal to amplifier gain control circuits. A pickup microphone detects audible sounds from a patient and produces an output signal representative thereof, and a variable gain amplifier amplifies the output signal of the pickup microphone. The amplifier drives an acoustic transducer in a headset which converts the amplified signal to audible sounds for audible detection by the user. A feedback microphone is placed near the acoustic transducer to detect the audible sounds produced thereby, and provides a feedback output signal. A control circuit compares the feedback output signal with the output signal produced by the pickup microphone, and in dependence thereon controls the transfer function of the variable gain amplifier, such that the audible output of the acoustic transducer is substantially the same as the audible input to the pickup microphone.

10 Claims, 7 Drawing Figures

ELECTRONIC STETHOSCOPE

BACKGROUND OF THE INVENTION

1. Field of the Invention

The present invention relates generally to an electronic stethoscope, and more particularly pertains to an electronic stethoscope which produces an audible output response having frequency components and characteristics which accurately match those of the initially detected auscultatory sounds.

2. Discussion of the Prior Art

The inherent promise embodied in an electronic stethoscope is that it will match the tonal qualities of a standard flexible tubing stethoscope while reducing background and tubing noise, increasing the user's comfort, removing the risk of transmitting ear canal infections, allowing tape recording and conferencing among multiple users and compensating for a user's hearing loss. However, past commercial attempts to produce an electronic stethoscope have received little enthusiasm from the medical community because these units had significantly different frequency response characteristics when compared to standard rubber tubing stethoscopes, and also introduced objectionable signal distortion and background noise. To gain medical acceptance, an electronic stethoscope should sound the same to physicians who are trained and practiced in recognizing audio cues which are transmitted by an auscultation instrument. This requirement to recreate the sound of a given standard stethoscope is a taxing one from an engineering point of view.

The realistic reproduction of clinically important audible signals pushes currently available audio equipment to the limit by requiring high level, distortion-free response down to the subsonic range. An electronic stethoscope should have a wide dynamic range with a low noise level to satisfy the wide dynamic range, keen discrimination, and high sensitivity of the human ear. The audible portion of the frequency spectrum of heart sounds has been reported to be 40–500 Hz, and for Korotkoff sounds, the range is 20–300 Hz. The greatest energy of these signals is contained in the lowest frequencies, with resting heart sound pressure levels reported to be 80 dB-SPL (0 dB-SPL at 0.0002 dyne/cm$^2$) at 20 Hz.

Kimball, et al. U.S. Pat. No. 4,220,160 discloses, for example, an electronic stethoscope in which detected audible heart sounds at sonic and subsonic frequencies are detected and converted into somewhat corresponding electrical signals, which are then transposed in frequency to a range more easily detectable by the human ear. The new frequency range can also be suitable for transmission over conventional phone lines, for discrimination of low intensity or brief heart sounds, and for the display of the heart sounds on conventional visual recording devices such as, cardiographs, storage oscilloscopes, and chart recorders. The transposition of the heart sound frequency components involves the addition of a constant frequency component to all of the heart sound frequency components in such a manner as to preserve the characteristics of the heart sound frequency components. The transposer circuit employs a voltage multiplier circuit for multiplying the heart sound frequency components with a constant frequency component to provide sum and difference frequency components of the heart sounds. The sum and difference frequency components are then filtered to produce only the sum of the heart sounds, which is then amplified and presented to a conventional loudspeaker, headphone, audio system, phone line, tape recorder, or radio transmitter with suitable bandwidth, for aural interpretation. This electronic stethoscope is typical of other prior art electronic stethoscopes in that the amplifier is simply a high fidelity electrical amplifier which does not exactly reproduce at the user's ear the original sound signals from the patient, and also introduces distortions thereto in accordance with the transfer characteristics of the amplifier, an acoustic to electrical transducer, and an electrical to acoustic transducer.

SUMMARY OF THE INVENTION

Accordingly, it is a primary object of the present invention to provide an electronic stethoscope which reproduces at the user's ear as exactly as possible the sound pressure signals originating from any conventional diaphragm- or bell-type chestpiece.

A further object of the subject invention is the provision of a Dynamically Altering Transfer Audio (DATA) electronic stethoscope which implements an innovative electronic and acoustic design to achieve the full potential forseen for electronic stethoscopes while overcoming the past problems associated therewith. This unit is preferably a pocket-sized instrument with comfortable headphones and a microphone pickup capsule which is designed to attach to any conventional bell or diaphragm chestpiece. The DATA stethoscope is preferably free of volume and tonal adjustments, and provides a full required dynamic range without introducing harmonic distortion or background "hash" noise, while also reducing the ambient room noise reaching the physician. Advantageously, the DATA stethoscope can also have a calibrated (known millivolts per sound pressure level) output port, to which another DATA stethoscope or recording equipment can be connected.

The subject invention utilizes a signal processing approach which relies upon acousto-electronic feedback to provide an error or adjustment signal to amplifier gain control circuits, thus ensuring that the signal heard by the listener is as exact a reproduction of the ausculated signal as possible. This acousto-electronic feedback approach preferably utilizes pickup and feedback microphones having as closely identical characteristics as possible.

In accordance with the teachings herein, the present invention provides an electronic stethoscope which includes a pickup microphone for detecting audible sounds from a patient and for producing an output signal representative thereof. An automatic variable gain amplifier is coupled to amplify the output signal of the pickup microphone. The amplifier drives an acoustic transducer which converts the amplified signal to audible sounds for audible detection by a person utilizing the electronic stethoscope. A feedback microphone is placed near the acoustic transducer to detect the audible sounds produced thereby, and provides a feedback output signal.

A control circuit compares the feedback output signal with the output signal produced by the pickup microphone, and in dependence thereon controls the transfer function of the variable gain amplifier, such that the audible output of the acoustic transducer is substantially the same as the audible input to the pickup microphone. In this arrangement, the transfer function of the amplifier is controlled such that the feedback output signal of the feedback microphone is substantially equal to the output signal of the pickup microphone, which thereby compensates for the distortion characteristics of the microphones and headphone. The pickup microphone and the feedback microphone are substantially identical microphones, and preferably are condenser electret microphones. In this arrangement, conceptually since the microphones are as identical as possible with identical distortion characteristics, then by controlling the amplifier transfer characteristics such that the microphone output signals are as identical as possible, the audible output of the acoustic transducer is driven to be as identical as possible to the audible input to the pickup microphone. In this arrangement, the headphones are preferably suspended planar diaphragm headphones which have superior harmonic and resonance characteristics.

In the preferred embodiment, the transfer characteristic of the amplifier is varied by providing amplification through a plurality of different bandpass amplifiers. In one preferred embodiment, a low frequency amplifier is provided with a relatively high gain factor, a high frequency amplifier is provided with a relatively low gain factor, and an intermediate frequency amplifier has a gain factor somewhere between the high and low gain factors, such that the low frequency portion of the signal spectrum, which is very important for medical analysis, is provided with the greatest signal energy. In the disclosed embodiment, the low frequency amplifier has a bandpass from 15 to 40 hertz with a gain factor of approximately 8 dB, the intermediate frequency amplifier has a bandpass from 40 to 100 hertz with a gain factor of approximately 6 dB, and the high frequency amplifier has a bandpass from 100 to 1000 hertz with a gain factor of approximately 0 dB.

The embodiment disclosed herein was designed to be utilized with a conventional diaphragm or bell type chestpiece for detecting auscultatory sounds. However, the teachings herein have broad applicability for the detection of many different types of sounds.

Moreover, in accordance with another advantageous feature of the present invention, a compensating circuit is provided to enable the transfer function of the variable gain amplifier to be varied to compensate for the particular hearing loss characteristics of a particular person, which could be a significant feature. Since the response characteristics of the DATA stethoscope can be varied or selected, the inverse response characteristics of the user's hearing loss response characteristics can be selected in a special DATA stethoscope unit such that the resultant sound heard by the user is substantially the audible sound originating at the chestpiece.

Another advantageous feature of the present invention is the provision of a trainer/conference, input/output port, which expands the medical utility of the electronic stethoscope. The port enables a calibrated (known millivolts per sound pressure level) tape recording of the auscultation signal, or sharing of the electrical output signal with a student or colleague possessing another DATA stethoscope, or other persons in the room could listen to the ausculated sounds by connecting the trainer output to an audio amplifier with speakers having a sufficient bass response.

BRIEF DESCRIPTION OF THE DRAWINGS

The foregoing objects and advantages of the present invention for an electronic stethoscope may be more readily understood by one skilled in the art with reference being had to the following detailed description of a preferred embodiments thereof taken in conjunction with the accompanying drawings wherein like elements are designated by identical reference numerals throughout the several views, and in which.

DETAILED DESCRIPTION OF THE DRAWINGS

Figures 1, 2:
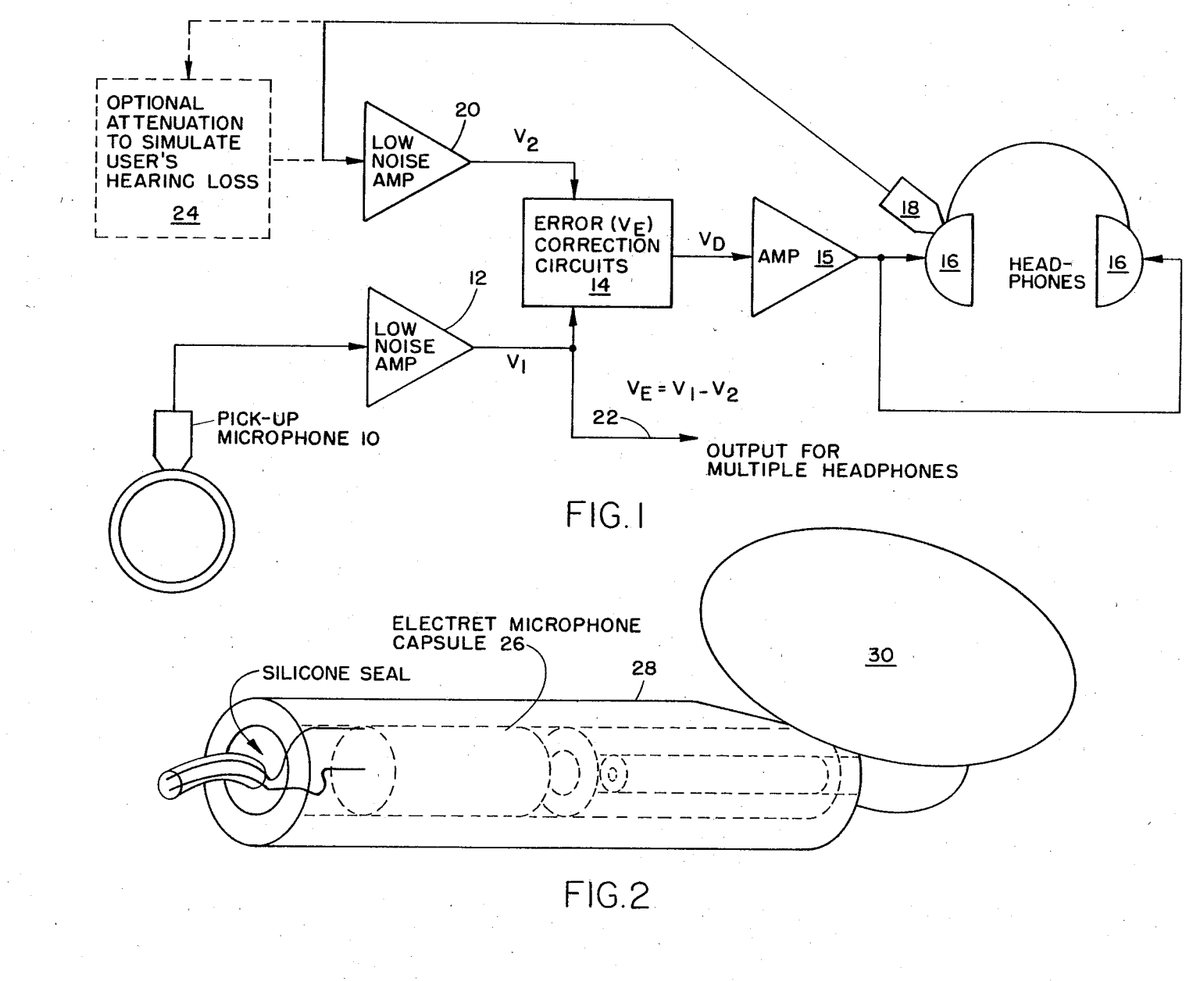
FIG. 1 is a block diagram of an exemplary embodiment of a embodiment of an electronic stethoscope constructed pursuant to the teachings of the present invention.
FIG. 2 illustrates one exemplary embodiment of a coupler assembly for mounting an acoustical pickup microphone relative to a conventional chestpiece coupler.

Referring to the drawings in detail, FIG. 1 illustrates a block diagram of a preferred embodiment of an electronic stethoscope pursuant to the present invention in which a pickup acoustical microphone transducer 10 is mounted relative to a chestpiece to detect auscultatory sounds from a patient through a conventional diaphragm or bell-type chestpiece. The output from the transducer 10 is directed through a preamplifier 12 to a control circuit variable gain amplifier 14, the transfer characteristics of which are controlled as described hereinbelow. The variable gain amplifier 14 is coupled to a power amplifier 15 which then drives a headphone acoustic transducer 16 of a headset. The headphone acoustic transducer 16 is preferably a suspended planar diaphragm type of headphone. A feedback microphone 18 is placed in the headset near the acoustic transducer 16 to detect its audible output, and provides a feedback output signal to a further preamplifier 20 which is coupled as a second input to the control circuit 14.

The control circuit 14 compares the feedback output signal from feedback microphone 18 and preamplifier 20 with the output from the pickup microphone 10 and preamplifier 12, and controls the transfer function of the variable gain amplifier 14 such that the audible output of the acoustic transducer is as identical as possible to the audible input to the pickup microphone. In this arrangement, the transfer function of the amplifier is controlled such that the feedback output signal of the feedback microphone is substantially equal to the output signal of the pickup microphone, which compensates for the distortion characteristics of the microphones and headphones, including the distortion characteristics of the pickup microphone 10, the acoustic transducer 16, and the feedback microphone 18. The pickup microphone and the feedback microphone are substantially identical microphones, and preferably are condenser electret microphones. Conceptually, since the microphones are as identical as possible with identical distortions, then by controlling the amplifier 14 transfer characteristics such that the microphone 10, 18 output signals are as identical as possible, the audible output of the acoustic transducer 16 is driven to be as identical as possible to the audible input to the pickup microphone 10.

The electronic stethoscope includes a trainer/conference input/output port 22, which greatly enhances or expands the DATA stethoscope's medical utility. The port enables a calibrated (known millivolts per sound pressure level) tape recording of the auscultated input, or sharing of the signal with a student or colleague possessing another similar electronic stethoscope. Furthermore, other persons and colleagues could listen to the auscultated sounds by connecting the trainer output to an audio amplifier with associated speakers having a sufficient bass response.

One of the drawbacks to conventional acoustic stethoscopes is that only one person at a time can listen to them. Since it is very difficult to accurately describe the subjective experience of sound, it is difficult for new students to learn auscultatory techniques if they must match a teacher's description with what they themselves perceive. Similarly, physicians cannot always reach a consensus on what malady they observed singly with an acoustic stethoscope, and the disparities in their diagnoses are only aggravated by the need for imaginative descriptions merely to communicate what they heard. Both of these situations can be improved with the DATA electronic stethoscope since it has a special port to allow sounds auscultated with one device to be transmitted to another.

The trainer/conference port is designed to meet three criteria. First, it provides a calibrated (known millivolts per sound pressure level) output from the primary stethoscope which obtains the auscultated signal. Secondly, it is constructed so that electronic stethoscopes may serve interchangeably as the primary stethoscope or as the secondary stethoscope, with their respective roles established by a directionally dependent connector. The directional dependance is established by the interconnecting cable. The electronic stethoscope to which the source cable is connected becomes the source of acoustic information. The remaining connector is the listener connection. Thirdly, its presence must be transparent to the primary user, whether or not a secondary unit is attached.

Compensation for a user's hearing loss using the electronic stethoscope is another significant feature of the present invention. Since the response characteristics of the stethoscope can be controlledly changed, the inverse response characteristics of a user's hearing loss response characteristics can be selected in a compensating circuit 24 such that the resultant sound heard by the user is the same as the sound originating at the chestpiece. For instance, the compensating circuit 24 can selectively attenuate different frequencies such that those frequencies are later amplified to a greater extent by the variable gain control circuit 14. The compensating circuit can be simply parallel bandpass filters feeding a separately adjustable potentiometer for each bandpass, with the outputs of the separate potentiometers being summed and combined again for an input to the variable gain circuit 14.

FIG. 2 illustrates a preferred embodiment of a chestpiece coupler in which a pickup microphone 10 is preferably a low noise electret cartridge 26 (Sony model EC-1) excised from a commercially supplied case and sealed in a cylindrical capsule 28, 1.4 cm in diameter and 5 cm long, into which a chestpiece 30 is also inserted.

The chestpiece coupler serves as an interface between standard auscultatory equipment and the electronic stethoscope. Two simple user-oriented objectives for this coupler were to make it compatible with any auscultatory chestpiece, and to make it similar to a conventional stethoscope in feel and in ease of use. Two performance criteria were that the coupler should have good low frequency response and an inaudible noise contribution. The chestpiece coupler which was designed with these considerations is a plastic tubing shell which houses a microphone cartridge and admits a 3/16" outer diameter (o.d.) chestpiece stem, (FIG. 2). The overall size of the chestpiece coupler is 2 ¼" long by ⅜" diameter. It is constructed from a 1" length of 3/16" inner diameter (i.d.) plastic tubing (Cole Parmer 6408-45) which is fixed inside a 2 ¼" length of ⅜" i.d. tubing (Tyson R-3603).

The microphone cartridge is mounted in the ⅜" tubing ¼" from the end of the 3/16" tubing. The cartridge and lead dressing take up the 1" remaining in the ⅜" tube, and the output leads are set in a silicone sealant. The electrical cable is preferably a 3' length of two-lead shielded cable terminated by a subminiature phono plug.

In the disclosed embodiment, a Sony EC-1 Electret Condenser Microphone was selected for the pickup microphone on the basis of its very low noise performance compared with other available microphones. A commercial microphone was disassembled, and the microphone cartridge was removed for use in the present invention. The microphone was mounted inside the direct-coupled, sealed case, and achieved a flat ($+/-1$ dB) frequence response down to 30 Hz, and unit to unit variation was within 2 dB. This represents a considerable improvement in low frequency response beyond the commercial form of the microphone assembly.

Figure 6:
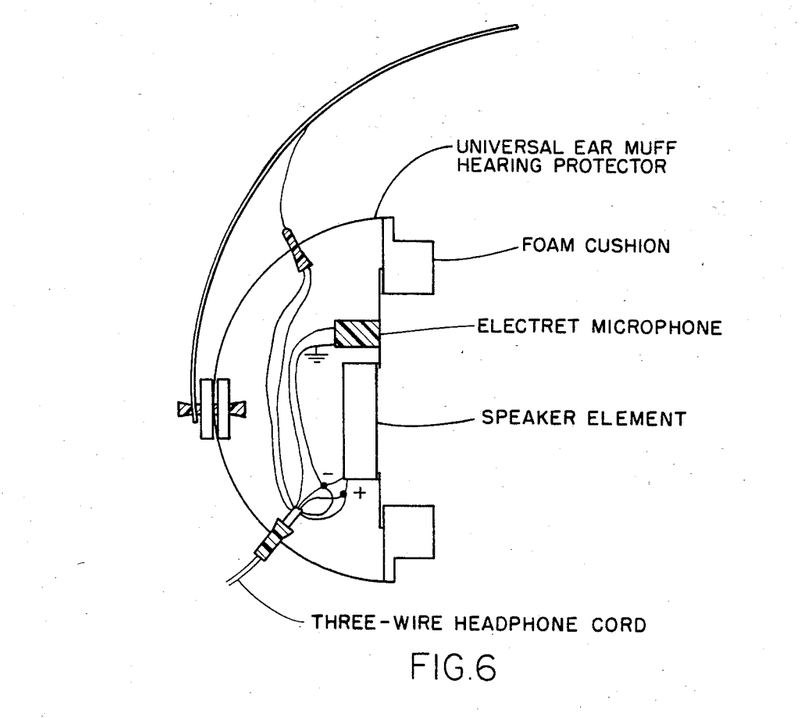
FIG. 6 illustrates one exemplary embodiment of a headphone for use with the present invention.

In the preferred embodiment, the headphones 16 are preferably planar diaphragm speaker elements (Radio Shack Realistic Model PRO-30) removed from their commercial headset and mounted in a hearing protector headset (Bilson Universal Ear Muff) along with a second closely matched EC-1 electret microphone 18, which provides ambient noise reduction and a well-sealed environment for the planar speakers to produce low frequency sounds. These components and mountings were chosen to maximize the low frequency capabilities, and the signal processing circuits described herein are also designed and employed to remedy their residual deficiencies. This signal processing relies on acousto-electronic feedback to provide the error signal to the gain control circuits, thus ensuring that the signal heard by the listener is as exact a reproduction of the auscultated signal as possible. The acousto-electronic feedback principle requires that the pickup and feedback microphones have as identical characteristics as possible.

The second Sony EC-1 microphone cartridge mounted in the headphones provides a feedback signal which is a measure of the acoustic response realized by the system and heard by the user. As will be described in more detail hereinbelow, this feedback is used to adjust the system's gain so that the output of the feedback microphone matches as closely as possible the output of the chestpiece microphone. In practice, the output characteristics of the two microphones are matched as closely as possible from commercially available similar components.

Figure 3A:
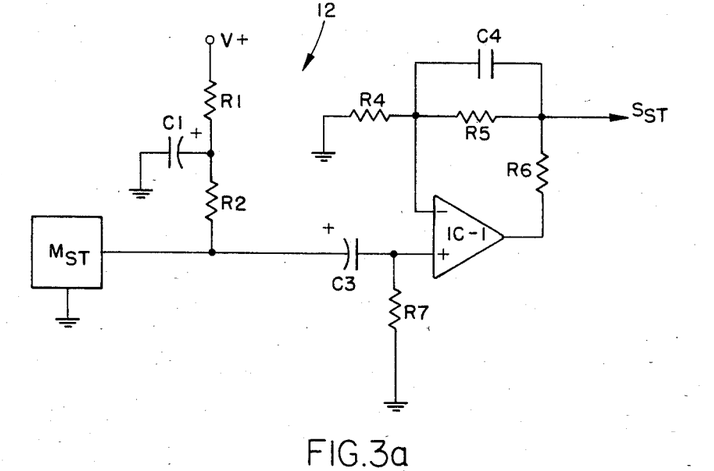
FIGS. 3a and 3b illustrate exemplary schematics of preamplifier circuits for use with the present invention.
Figure 3B:
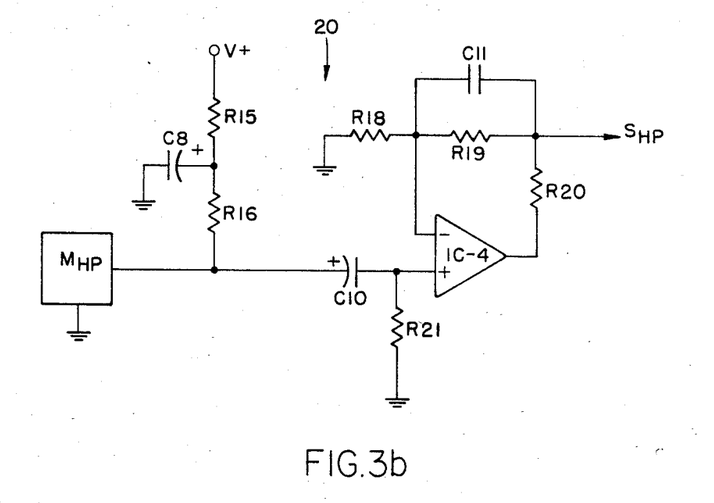

The preamplifiers 12, 20 can be simply two matched, high gain, low noise amplifiers which provide gain for the two microphones 10, 18 of matched sensitivity. The two substantially identical circuits of FIG. 3, with the individual electrical components and integrated circuits given in the Table of Component Values herein, are suitable for preferred embodiments of the present invention.

Figure 4:
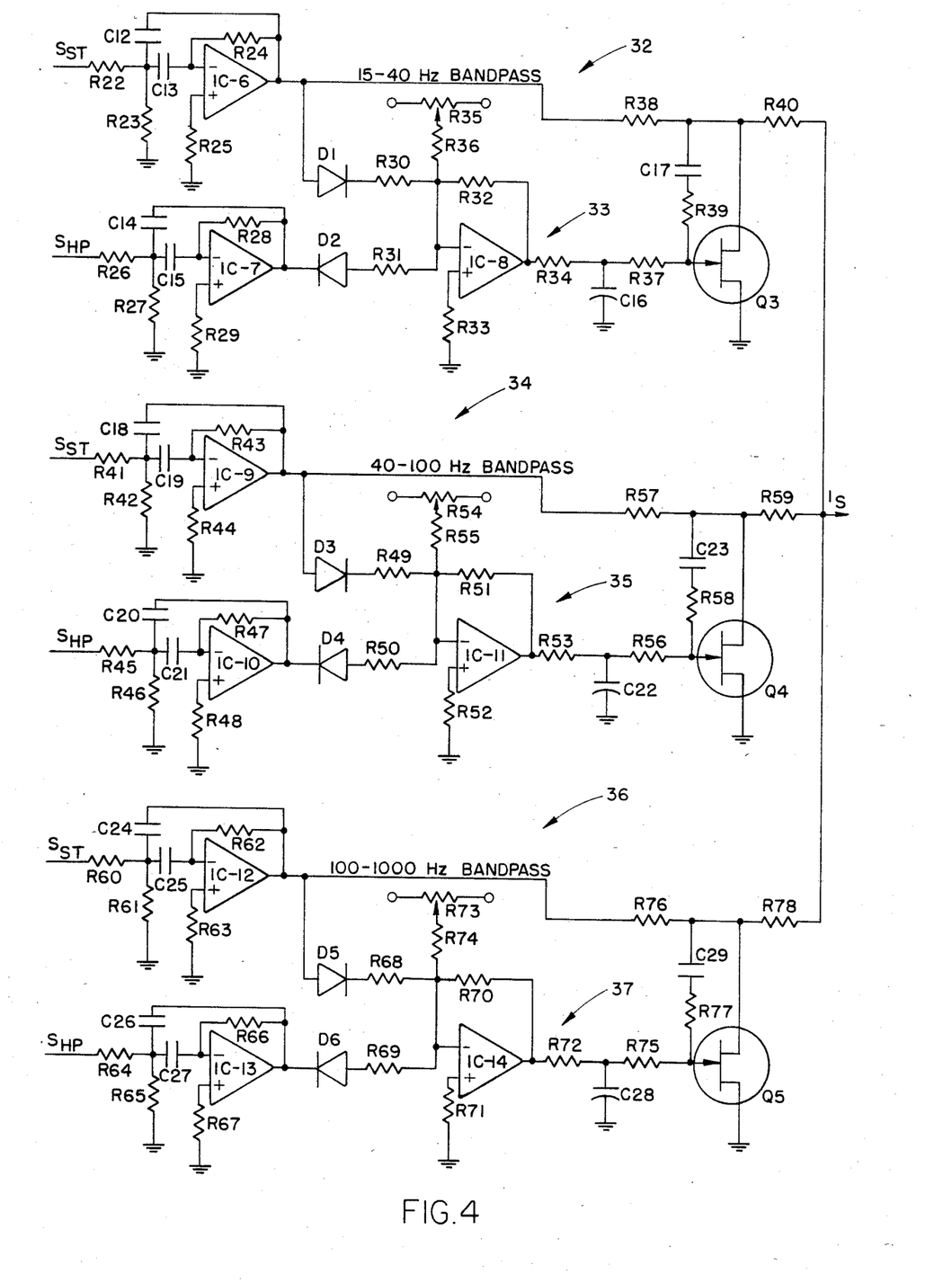
FIG. 4 is a schematic illustration of three adjacent bandpass amplifier circuits having automatic gain control circuits for varying the transfer characteristics of the amplifiers.

In a preferred embodiment, the transfer characteristic of the amplifier section 14 is varied by providing amplification through a plurality of different, adjacent bandpass amplifiers. In one preferred embodiment, a low frequency amplifier is provided with a relatively high gain factor, a high frequency amplifier is provided with a relatively low gain factor, and an intermediate frequency amplifier has a gain factor somewhere between the high and low gain factors, such that the low frequency portion of the signal spectrum, which is very important for medical analysis, is provided with the greatest amplification and signal energy. In the disclosed embodiment, the low frequency amplifier has a bandpass from 15 to 40 hertz with a gain factor of approximately 8 dB, the intermediate frequency amplifier has a bandpass from 40 to 100 hertz with a gain factor of approximately 6 dB, and the high frequency amplifier has a bandpass from 100 to 1000 hertz with a gain factor of approximately 0 dB.

Referring in particular to FIG. 4, the signal processing task is shared by three parallel bandpass sections 32, 34, and 36, which together cover the entire spectrum of interest of auscultated sounds. The gain of each particular bandpass section is regulated by an automatic gain control circuit, respectively 33, 35 and 37. These bandpass sections compensate for variations in acoustic loading at the headphones and also for frequency distortion caused by the pick-up microphone and the headset speakers. The three bandpass sections also allow a greater emphasis on the low frequencies since this portion of the signal spectrum encompasses both the greatest auscultation signal energy (a typical auscultation signal has its largest sound pressure levels at its lower frequencies) and the weakest headphone response. The gain control circuits 33, 35 and 37 compare the auscultatory input level and the acoustic output level and adjust the gain of each bandpass section to minimize the error. A quiescent gain level is established by potentiometers R35, R54 and R73 in the absence of an ausculated input signal. Because of the low repetition rate of the ausculated signals, the gain control circuits have a 2 second time constant. Each gain control section has a dynamic range of 20 dB, which is sufficient to correct the remaining errors in the pickup microphone and the speaker response characteristics. Separate quiescent gain and variable gain control is used for each section so that the sum of all three sections yields a close approximation to a flat frequency response for the entire electronic stethoscope system.

The bandpassing is implemented in FIG. 4 using single stage two-pole filters, of which the configuration for IC-6 is a good example. Each chestpiece bandpass filter has a matching feedback bandpass filter. This is necessary for computing a true error level between the chestpiece and feedback inputs within each bandpass.

The 15–1000 Hz range is divided into three subranges of 15–40 Hz, 40–100 Hz, and 100–1000 Hz, with selected maximum gains of 8 dB for the 15–40 Hz section, 6 dB for the 40–100 Hz, and 0 dB for the 100–1000 Hz. The overlay of the rolloff regions and the adjoining bandpass sections results in the actual gain being higher than the specified gain. Examination of the headset response shows that the bandpass regions and chosen gains are well suited for equalizing the low frequency response.

A very important feature of this electronic stethoscope design is the use of acousto-electronic feedback to regulate the headphone output so that it more nearly matches the chestpiece coupler input, despite variations in the frequency response of the chestpiece microphone and the headphone due to resonances and attenuation. A significant feature of the automatic gain control circuitry is that it corrects for the poor low frequency response of headphones in the critical 20–50 Hz region. The automatic gain control also adjusts for limited variations in the quality of the seal achieved at the earcushions of the headset.

Gain control of 20 dB is achieved by using a single JFET and some additional passive components in the circuit shown in FIG. 4. JFETs Q3, Q4, and Q5, one for each bandpass section, all share the same design and nearly the same component values. Using Q3 of the 15–40 Hz bandpass section as an example, the JFET is used as a Voltage Variable Resistor (VVR) with resistor R40 in a current divider network. As the Gate-to-Source Voltage (VGS) on Q3 is increased above about −2.0 V, the JFET begins to turn on and its Drain-to-Source resistance decreases. Consequently, this VVR shunts some of the signal to ground that would otherwise go through R40 into the summing junction of IC-15. As the VGS becomes more positive, more signal current (Is) is drawn away, decreasing the voltage gain achieved at the output of IC-15.

For the JFET to provide a linear change in resistance with varying VGS and Drain-to-Source voltage (Vds) bias, it must be operated with Vds near zero. In practice, this turns out to be Vds of 0.2 V P-P. To keep Vds in this range, it is necessary to form a voltage divider with R38 and R40 to limit Vds to this value for maximum signal levels (assumed to be 10.0 V P-P for 15–40 Hz, 7.4 V P-P for 40–100 Hz, and 3.6 V P-P for the 100–1000 Hz bandpass). Linearity of the JFET is also maintained by the AC feedback provided by C17 and R39.

The quiescent value of the gain control amplifier is set by R35 to about −1.6 V. This level is a prudent choice as it falls about in the middle of the gain versus VGS curve, and it gives a value of RDS large enough to prevent quiescent hash noise generated by the gain control amplifier from being audible. C31 on the summing amplifier (IC-15) is provided to attenuate any noise above 1 kHz.

The dynamic value for gain control is varied around the set point by the action of the automatic gain control level amplifier. This amplifier sums the oppositely-phased, half-wave rectified outputs of the chestpiece and feedback preamplifiers. Their overall amplitude difference is thus obtained and, greatly amplified, is used to charge a large capacitor, C16, with a 2-second time constant. As the feedback signal amplitude falls below the chestpiece input signal over time (this time constant is dictated by the heart rate), more gain is called for by decreasing VGS.

Figure 5:
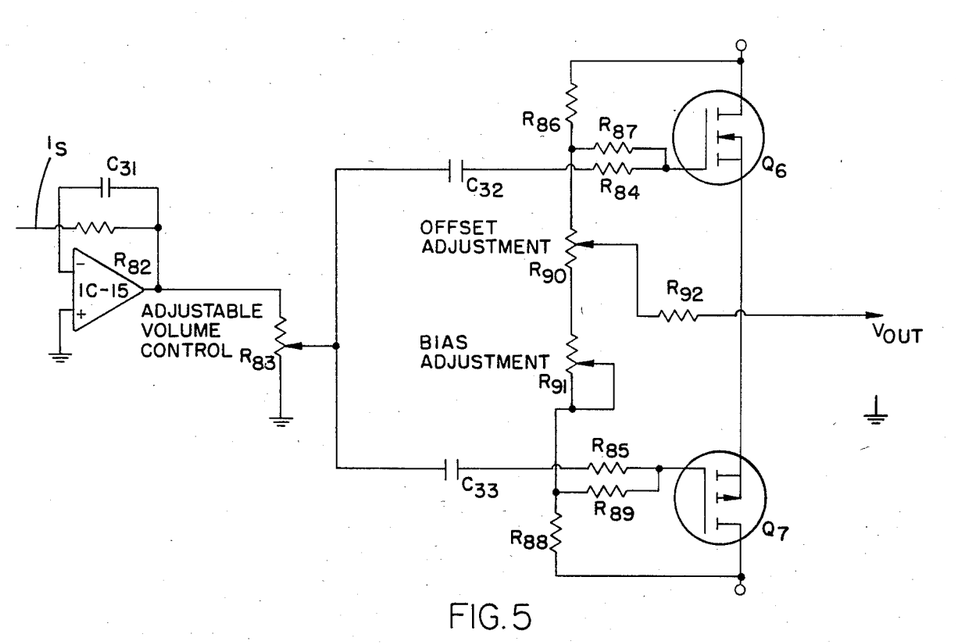
FIG. 5 is an exemplary schematic circuit of a summing and power amplifier circuit which is coupled to the output of the variable gain amplifier of FIG. 4.

The output signal of the bandpass amplifiers of FIG. 4 is directed to a summing and power amplifier circuit as shown in FIG. 5. The output of the summing amplifier IC-15 (FIG. 5) is the completely processed chestpiece signal. The additional amplifier stage provides the high current drive required by the headphones. This amplifier should be suitable for a battery-powered instrument, have low quiescent power consumption, being capable of driving an 8 ohm headset, have a flat frequency response over the 15–1000 Hz range, and have inaudible noise and cross-over distortion. A preferred power amplifier, FIG. 5, is an AC-coupled input, class AB power amplifier with a DC-coupled output. This simple amplifier uses only two active components, a pair of complementary power MOSFET's (IFR 520 and IRF 9520). The bias network is a trimmed resistive configuration (R86–92), which is adjusted so that the amplifier draws only 15 mA when quiescent. Another trim potentiometer (R90) is used to set the output DC level to 0 Volts.

The amplifier has 0 dB of gain in a no-load situation, but is only down −2.5 dB for an 8 ohm load even beyond the rated full scale output of 10 V P-P. This power amplifier exhibits a flat (+/−1 dB) response with negligible distortion from 4 Hz to 100 kHz into 8 ohms.

Power consumption is preferably maintained as low as possible so the electronic stethoscope is battery-powered and sufficiently portable and small to be placed in a pocket. The strenuous power demands of the headphones, however, necessitate a battery pack with a moderately high current rating. In one constructed embodiment of the present invention, the stethoscope circuitry and a rechargeable battery pack were mounted in a pocket-sized, 13.8×8.3×2.8 cm case. The total weight of the case and headphones was 780 grams, and the battery pack had enough power for 10 hours of operation before recharging.

Harmonic distortion that accompanys the headphone response at low frequency, high intensity outputs appears to be an inherent problem with dynamic-type headphones. Fortunately, a new type of speaker element is available which, similar to electro-static speakers, uses a single thin planar diaphragm to produce sound waves with very little harmonic distortion, even in the 25–50 Hz range. These planar-type headphones are available as the Realistic PRO 30, by Radio Shack. They had less perceptible harmonic distortion than other tested dynamic headphones, but when measured, their response and harmonic distortion seemed similar to that of the dynamic types. In a preferred embodiment, the speaker elements were removed from the PRO 30's and they were mounted in a pair of supra-aural hearing protectors such as Bilsom Comflex or Bilsom Universal ESR hearing protectors. The tight seal provided by the hearing protectors improved the low frequency response, and the reduction in ambient noise served to further increase the signal to noise ratio.

The circuitry of the electronic stethoscope was designed to complement the frequency response of this headset. The 8 and 6 dB quiescent gain provided by the 15–40 and 40–100 Hz bandpass sections offset the headphone's loss in these areas.

The following Table of Component Values lists particular values for the circuit components of FIGS. 3, 4 and 5 in one designed embodiment thereof.

Table of Component Values
ACTIVE DEVICES
IC1,4  (¼) TL074 Quad Low Noise BiFET Op Amp -continued
Table of Component Values

| | |
|---|---|
| IC6-15 | (¼) 4741 Quad Op Amp |
| Q3–5 | 2N4220A Low Noise, Gen Purp JFET |
| Q6 | IRF 520 N-Channel power HOSFET |
| Q7 | IRF 9520 P-Channel power MOSFET |
| D1–6 | IN4148 |

RESISTORS

| Chestpiece Preamp | | Feedback Preamp | | | |
|---|---|---|---|---|---|
| R1 | 9.1K | R15 | 9.1K | | |
| R2 | 9.1K | R16 | 9.1K | | |
| R4 | 2.0K | R18 | 2.0K | | |
| R5 | 51.K | R19 | 51.K | | |
| R6 | 2.0K | R20 | 2.0K | | |
| R7 | 200K | R21 | 200K | | |
| BandPass 1 | | BandPass 2 | | BandPass 3 | |
| R22,26 | 51.K | R41,45 | 68.K | R60,64 | 150K |
| R24,28 | 270K | R43,47 | 270K | R62,66 | 180K |
| R25,29 | 270K | R44,48 | 270K | R63,67 | 180K |
| R30,31 | 150K | R49,50 | 150K | R68,69 | 150K |
| R32 | 75.K | R51 | 75.K | R70 | 2.0 M |
| R33 | 75.K | R52 | 75.K | R71 | 75.K |
| R34 | 200K | R53 | 200K | R72 | 200K |
| R35 | 500K Pot | R54 | 500K Pot | R73 | 500K Pot |
| R36 | 510K | R55 | 510K | R74 | 1.0 M |
| R37 | 1.0 M | R56 | 1.0 M | R75 | 1.0 M |
| R38 | 100K | R57 | 100K | R76 | 91.K |
| R39 | 1.0 M | R58 | 1.0 M | R77 | 1.0 M |
| R40 | 2.0K | R59 | 3.0K | R78 | 10.K |
| Output Amplifier | | | | | |
| R82 | 100K | | | | |
| R84,85 | 100 | | | | |
| R86,88 | 500K | | | | |
| R87,89 | 1.0 M | | | | |
| R90 | 1.0 M Pot | | | | |
| R91 | 500K Pot | | | | |
| R92 | 100 | | | | |

Capacitors

| Chestpiece Preamp | | Feedback Preamp | | | |
|---|---|---|---|---|---|
| C1,3 | 10 uF | C8,10 | 10 uF | | |
| Deleted: C2,4–7,9,11,30 | | | | | |
| BandPass 1 | | BandPass 2 | | BandPass 3 | |
| C12,14 | .05 uF | C18,20 | .02 uF | C24,26 | .001 uF |
| C13,15 | .05 uF | C19,21 | .02 uF | C25,27 | .015 uF |
| C16 | 10. uf | C22 | 10. uF | C28 | 10.0 uF |
| C17 | .05 uF | C23 | .05 uF | C29 | 0.05 uF |
| Output Amplifier | | | | | |
| C31 | 500 pF | | | | |
| C32,33 | .0068–.05 uF | | | | |

Evaluation of the ability of a preferred embodiment of an electronic stethoscope as described herein to emulate a standard stethoscope was carried out through both objective acoustical measurements and subjective clinical evaluations. An operative embodiment of a electronic stethoscope was given to several clinical physicians and research physiologists for subjective evaluation of its use for heart sounds and blood pressure measurements. The subjective evaluations for users experienced in the use of conventional stethoscopes were generally very favorable. All users expressed the opinion that the sound quality of the electronic stethoscope was equal to that of a conventional stethoscope. Several users expressed very favorable opinions about the comfort of the headsets, the conferencing feature for multiple listeners, the elimination of motion-induced noise by elimination of the conventional tubing, and possibility for hearing loss compensation. All simultaneous blood pressure measurements using the electronic and conventional stethoscopes produced equal results.

While several embodiments and variations of the present invention for an electronic stethoscope are described in detail herein, it should be apparent that the disclosure and teachings of the present invention will suggest many alternative designs to those skilled in the art.

What is claimed is:

1. An electronic stethoscope, comprising:
   a. a pickup microphone for detecting audible sounds from a patient and for producing an output signal representative thereof;
   b. a control circuit including a variable gain amplifier means coupled to the output signal of said pickup microphone for amplifying the signal, said variable gain amplifier means having a dynamically controllable transfer function;
   c. at least one acoustic transducer coupled to said amplifier for converting the amplified signal to audible sounds for audible detection by a person utilizing the electronic stethoscope;
   d. a feedback microphone for detecting the audible sound produced by said acoustic transducer and for providing a feedback output signal representative thereof; and
   e. said control circuit comparing said feedback output signal with the output signal produced by said pickup microphone to dynamically control the transfer function of said variable gain amplifier, such that the audible output of the acoustic transducer is substantially the same as the audible input to the pickup microphone.

2. An electronic stethoscope as claimed in claim 1, said pickup microphone being coupled to a pick-up unit for detecting ausculatory sounds from a patient, and said acoustic transducer being mounted in a headset.

3. An electronic stethoscope as claimed in claim 1, wherein the transfer function of said variable gain amplifier is controlled such that the feedback output signal of said feedback microphone is substantially equal to the output signal of said pickup microphone, to compensate for the distortion characteristics of said pickup microphone.

4. An electronic stethoscope as claimed in claim 1, wherein said pickup microphone and said feedback microphone are substantially identical microphones.

5. An electronic stethoscope as claimed in claim 4, said pickup and feedback microphones comprising condenser electret microphones.

6. An electronic stethoscope as claimed in claim 1, said variable gain amplifier means comprising a plurality of different bandpass, variable gain amplifiers.

7. An electronic stethoscope as claimed in claim 6, said plurality of different bandpass amplifiers comprising at least a low frequency amplifier having a relatively high gain factor, a high frequency amplifier having a relatively low gain factor, and an intermediate frequency amplifier having a gain factor between said high and low gain factors, such that the low frequency portion of the signal spectrum comprises the greatest signal energy.

8. An electronic stethoscope as claimed in claim 7, said low frequency amplifier having a bandpass of substantially 15 to 40 hertz and a gain factor of substantially 8 dB, said intermediate frequency amplifier having a bandpass of substantially 40 to 100 hertz and a gain factor of substantially 6 dB, and said high frequency amplifier having a bandpass of substantially 100 to 1000 hertz and a gain factor of substantially 0 dB.

9. An electronic stethoscope as claimed in claim 1, said control circuit including a compensating means to enable the transfer function of said variable gain amplifier means to be varied to compensate for the particular hearing loss characteristics of a particular person.

10. An electronic stethoscope as claimed in claim 1, further including an auxiliary output port to enable the output signal to be utilized for an auxiliary function.

* * * * *